(12) United States Patent
Cui (10) Patent No.: US 11,962,348 B2
(45) Date of Patent: Apr. 16, 2024

(54) AUDIOMETER SYSTEM WITH LIGHT-BASED COMMUNICATION

(71) Applicant: Natus Medical Incorporated, Orlando, FL (US)

(72) Inventor: Ningzhou Cui, Fox River Grove, IL (US)

(73) Assignee: Natus Medical Incorporated, Middleton, WI (US)

( * ) Notice: Subject to any disclaimer, the term of this patent is extended or adjusted under 35 U.S.C. 154(b) by 329 days.

(21) Appl. No.: 17/455,418

(22) Filed: Nov. 18, 2021

(65) Prior Publication Data

US 2023/0153053 A1    May 18, 2023

(51) Int. Cl.
*H04B 10/40* (2013.01)
*A61B 5/12* (2006.01)
*H04R 25/00* (2006.01)

(52) U.S. Cl.
CPC .............. *H04B 10/40* (2013.01); *A61B 5/12* (2013.01); *A61B 5/121* (2013.01); *H04R 25/70* (2013.01)

(58) Field of Classification Search
CPC .......... A61B 5/12; A61B 5/121; H04R 25/70; H04R 25/502
USPC ........................................................... 73/585
See application file for complete search history.

(56) References Cited

U.S. PATENT DOCUMENTS

| | | | |
|---|---|---|---|
| 9,094,768 B2* | 7/2015 | LaBosco | H04R 29/001 |
| 9,497,530 B1* | 11/2016 | Campbell | H04R 1/1091 |
| 9,729,970 B2* | 8/2017 | Udesen | H04R 25/552 |
| 10,460,095 B2* | 10/2019 | Boesen | H04R 1/1041 |
| 11,304,013 B2* | 4/2022 | Burwinkel | H04R 3/04 |
| 11,665,488 B2* | 5/2023 | Greenberg | A61B 5/7264 381/314 |
| 11,689,836 B2* | 6/2023 | Meyberg Guzman | H04R 1/08 381/74 |
| 11,800,302 B2* | 10/2023 | Harlander | H04R 25/55 |
| 11,818,545 B2* | 11/2023 | Usher | H04R 25/70 |

(Continued)

FOREIGN PATENT DOCUMENTS

| | | | | |
|---|---|---|---|---|
| CN | 112491470 A | * | 3/2021 | |
| DK | 2109934 T3 | * | 8/2016 | H03G 9/005 |

(Continued)

OTHER PUBLICATIONS

Matthew Lucas et al., Effects of earlens lens placement on sound field thresholds, tympanometric measurements and wideband acoustic immittance, Neuroscience Institute Publications, Jan. 1, 2022, p. 12 (Year: 2022).*

(Continued)

*Primary Examiner* — Stephanie E Bloss
*Assistant Examiner* — Kevin C Butler
(74) *Attorney, Agent, or Firm* — Daniel C. Pierron; Widerman Malek, PL (57) ABSTRACT

An audiometer system including an audiometer device that includes an audiometer digital signal processing (DSP) unit, an audiometer baseband processing unit positioned, and an (Continued)

audiometer light-based transceiver. The system further includes a transducer including a transducer light-based transceiver in optical communication with the audiometer light-based transceiver, a transducer baseband processing unit, a transducer processor unit, and an audio speaker.

20 Claims, 2 Drawing Sheets

(56) References Cited

U.S. PATENT DOCUMENTS

| | | | | |
|---|---|---|---|---|
| 2004/0254753 | A1* | 12/2004 | Bengtsson | A61B 5/12 73/1.82 |
| 2008/0165980 | A1* | 7/2008 | Pavlovic | H04R 5/04 381/60 |
| 2013/0303940 | A1* | 11/2013 | Saly | A61B 5/123 600/559 |
| 2018/0014107 | A1* | 1/2018 | Razouane | H04R 1/1083 |
| 2018/0124525 | A1* | 5/2018 | Mueller-Wehlau | G06F 16/683 |
| 2019/0289409 | A1* | 9/2019 | Greenberg | A61B 5/125 |
| 2023/0111715 | A1* | 4/2023 | Li | A61B 5/125 381/60 |
| 2023/0153053 | A1* | 5/2023 | Cui | H04B 10/114 700/94 |

FOREIGN PATENT DOCUMENTS

| | | | | |
|---|---|---|---|---|
| GB | 2555842 | A * | 5/2018 | A61B 5/121 |
| JP | 2018528735 | A * | 9/2018 | G06F 16/636 |

OTHER PUBLICATIONS

Perkins et al., The EarLens System: New SOund Transduction, Methods, National Institutes of Health, 2010, p. 23 (Year: 2010).*

Parth et al, Visible Light Communication, Networking, and Sensing: A Survey, Potential and Challenges by Pathak et al., IEEE Communications Surveys & Tutorials, vol. 17, No. 4, Fourth Quarter 2015 (Year: 2015).*

Francois Charih et al., Audiogram Digitization Tool for Audiological Reports, IEEE Access, Oct. 19, 2022, p. 9 (Year: 2022).*

Martinez-Baez, Manual and Automatic Programmable Audiomener, Annual International Conference of the IEEE Engineering in Medicine and Biology Society, vol. 13, No. 4, 1991, pp. 1915-1916 (Year: 1991).*

* cited by examiner

AUDIOMETER SYSTEM WITH LIGHT-BASED COMMUNICATION

FIELD OF THE INVENTION

The present invention relates to audiometry systems utilizing light-based communication between the audiometer and transducer devices.

BACKGROUND OF THE INVENTION

Audiometry requires the delivery of precise acoustic signals to generate similarly precise acoustic sounds in order to test the hearing of a patient. Original audiometry testing devices utilized entirely wired connections, where the audiometer device would generate a stimulus signal responsive to a user's input, and that signal would be transmitted over wired connection to the patient, usually without any intervening electronics. However, such systems necessary constrain the use of audiometry devices to either expensive permanent installations in dedicated rooms for audiometry or in portable systems with long, inconvenient, and cumbersome wiring that both limited the placement of audiometry equipment and necessarily constrained both the user and the patient to be in close physical proximity, which could cause undesired interference in terms of the patient possibly being able to hear or sense the user's actions, thereby potentially reducing the accuracy and effectiveness of the audiometry testing.

Radio-frequency (RF) devices have become more popular and enable wireless communication between computerized devices. However, RF communication suffers from a number of shortcomings that make its use in audiometry inappropriate. First, there is often noticeable latency in RF systems, which can exceed a maximum desirable latency of 200 milliseconds. Moreover, RF devices are more susceptible to interference owing to both their extensive use in electronic devices and their ability to penetrate typical walls in structures. Such interference may negatively impact the performance of the device or, in order to avoid such interference, may require enhanced encryption that would further increase the latency of such devices. Similarly, the security of RF devices is generally reduced with their ability to penetrate walls, thereby again necessitating encryption practices that reduce the performance of such devices and increases the cost.

Accordingly, there is a need in the art for an audiometry system that enables wireless audiometry without the disadvantages of RF communication. Light-based communication systems enables wireless communication while addressing the shortcomings of RF by having superior time performance (less latency) and greater security, as electromagnetic radiation within the IR, visible, and ultraviolet spectra generally does not penetrate walls and thus is less susceptible to interference and security concerns.

This background information is provided to reveal information believed by the applicant to be of possible relevance to the present invention. No admission is necessarily intended, nor should be construed, that any of the preceding information constitutes prior art against the present invention.

SUMMARY OF THE INVENTION

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes an audiometer device that may include an audiometer digital signal processing (DSP) unit configured to: generate stimulus signals responsive to a user input signal, and convert the stimulus signals to a plurality of stimulus data packets. The system also includes an audiometer baseband processing unit positioned in communication with the audiometer DSP unit and configured to convert the stimulus data packets to a plurality of stimulus audiometer frames. The audiometer may further include an audiometer light-based transceiver positioned in communication with the audiometer baseband processing unit and configured to transmit the plurality of stimulus audiometer frames. The system also includes a transducer that may include a transducer light-based transceiver positionable within a field of view of the audiometer light-based transceiver, the transducer light-based transceiver configured to receive the plurality of stimulus audiometer frames from the audiometer light-based transceiver, a transducer baseband processing unit positioned in communication with the transducer light-based transceiver and configured to convert the plurality of stimulus audiometer frames to a plurality of extracted stimulus data packets, a transducer processor unit positioned in communication with the transducer baseband processing unit and configured to convert the plurality of extracted stimulus data packets into a patient stimulus signal, and an audio speaker positioned in communication with the transducer processor unit and configured to generate a sound responsive to the patient stimulus signal. Other embodiments of this aspect include corresponding computer systems, apparatus, and computer programs recorded on one or more computer storage devices, each configured to perform the actions of the methods.

Implementations may include one or more of the following features. In some embodiments, the transducer further may include a transducer input device positioned in communication with the transducer processor unit and configured to receive a patient input from the patient, defining a received patient input, and generate a patient response signal from the received patient input; the transducer processor unit is further configured to convert the patient response signal to a plurality of transducer data packets. The transducer baseband processing unit may further be configured to generate a plurality of transducer frames, each transducer frame may include a transducer data packet. The transducer light-based transceiver may be further configured to transmit the plurality of transducer frames to the audiometer light-based transceiver. Additionally, the audiometer light-based transceiver may be further configured to receive the plurality of transducer frames from the transducer light-based transceiver. The audiometer baseband processing unit may be further configured to convert the plurality of transducer frames to a received patient audio signal stream. The audiometer DSP unit may be further configured to convert the received patient audio signal stream to an audio signal, defining a received patient audio signal, and transmit the received patient audio signal to a user playback device.

In some embodiments, the transducer light-based transceiver may be a first transducer light-based transceiver and the transducer is a first transducer, and the audiometer system may include a second transducer that may include a second transducer light-based transceiver positionable within a field of view of the audiometer light-based transceiver, the second transducer light-based transceiver configured to receive the plurality of audiometer frames from the audiometer light-based transceiver, a second transducer baseband processing unit positioned in communication with the second transducer light-based transceiver and configured to convert the plurality of audiometer frames to a second plurality of extracted stimulus data packets, a second transducer processor unit positioned in communication with the second transducer baseband processing unit and configured to convert the second plurality extracted stimulus data packets into a second patient stimulus signal, and a second audio speaker positioned in communication with the transducer processor unit and configured to receive the second patient stimulus signal from the transducer processor unit and generate a sound responsive to the second patient stimulus signal. The second transducer baseband processing unit may further be configured to receive the plurality of audiometer frames from the transducer light-based transceiver and extract the stimulus data packets from the audiometer frames, defining extracted stimulus data packets. The audiometer DSP unit may further be configured to generate a calibration data request may include a plurality of calibration data request packets. The audiometer baseband processing unit may be further configured to receive the plurality of calibration data request packets from the audiometer DSP unit and generate a plurality of calibration audiometer frames, each frame may include a packet of the calibration data request packets. Furthermore, the audiometer light-based transceiver may be further configured to transmit the plurality of calibration audiometer frames received from the audiometer baseband processing unit and the transducer light-based transceiver may be further configured to receive the plurality of calibration audiometer frames from the audiometer light-based transceiver. Additionally, the transducer baseband processing unit may be further configured to receive the plurality of calibration audiometer frames from the transducer light-based transceiver and extract the calibration data request packets from the calibration audiometer frames, defining a plurality of extracted calibration data request packets. The transducer processor unit may be further configured to receive the plurality of extracted calibration data request packets, parse the plurality of extracted calibration data request packets to extract the calibration data request therefrom, and read the calibration data stored in the transducer.

In some embodiments, the audiometer DSP unit may further be configured to receive at least one of an input audio signal and an input speech signal, defining an input signal, generate a stimulus stream responsive to the input signal, and generate a plurality of packets from the stimulus stream, defining stimulus data packets. Additionally, the audiometer baseband processing unit may further be configured to receive the stimulus data packets from the audiometer DSP unit and generate a plurality of stimulus audiometer frames, each frame may include a packet of the stimulus data packets. The transducer baseband processing unit may further be configured to receive the plurality of stimulus audiometer frames from the transducer light-based transceiver and extract the stimulus data packets from the stimulus audiometer frames, defining extracted stimulus data packets.

In some embodiment, the transducer further may include a transducer input device positioned in communication with the transducer processor unit and configured to: receive a patient input from the patient, defining a received patient input, and generate a patient response signal from the received patient input. The transducer processor unit may further be configured to receive the patient response signal from the transducer input device, generate a response data stream from the patient response signal, and generate a plurality of transducer data packets from the response data stream. Additionally, the transducer baseband processing unit may be further configured to receive the plurality of transducer data packets and generate a plurality of transducer frames, each transducer frame including a transducer data packet. The transducer light-based transceiver may be further configured to transmit the plurality of transducer frames to the audiometer light-based transceiver, and the audiometer light-based transceiver is further configured to receive the plurality of transducer frames from the transducer light-based transceiver Furthermore, the audiometer baseband processing unit is further configured to receive the plurality of transducer frames from the audiometer light-based transceiver and extract the plurality of transducer data packets from the transducer frames, defining a plurality of extracted transducer data packets. The audiometer DSP unit may be further configured to receive the plurality of extracted transducer data packets from the audiometer baseband processing unit, generate a received patient response signal stream from the plurality of extracted transducer data packets, convert the received patient response signal stream into an audio signal, defining a received patient audio signal, and transmit the received patient audio signal to a user playback device. The transducer input device may be at least one of an actuatable tactile device and a microphone. The user playback device may be at least one of an audio speaker and a computerized device.

In some embodiments, the transducer light-based transceiver is a first transducer light-based transceiver and the transducer is a first transducer. The audiometer DSP unit may be further configured to generate masking signals responsive to a user input masking signal and convert the masking signals to a plurality of masking data packets. The audiometer baseband processing unit may further be configured to: receive the masking data packets from the audiometer DSP unit and generate a plurality of masking audiometer frames, each frame may include a packet of the masking data packets. Additionally, the audiometer light-based transceiver may be further configured to transmit the masking audiometer frames received from the audiometer baseband processing unit. The audiometer system may further include a second transducer that may include a second transducer light-based transceiver positionable within a field of view of the audiometer light-based transceiver, the second transducer light-based transceiver configured to receive the plurality of masking audiometer frames from the audiometer light-based transceiver, a second transducer baseband processing unit positioned in communication with the second transducer light-based transceiver and configured to: receive the plurality of masking audiometer frames from the transducer light-based transceiver and extract the masking data packets from the audiometer frames, defining extracted masking data packets, a second transducer processor unit positioned in communication with the second transducer baseband processing unit and configured to: receive the extracted masking data packets and convert the extracted masking data packets into a masking signal, and a second audio speaker positioned in communication with the second transducer processor unit and configured to receive the masking signal from the transducer processor unit and generate a masking sound responsive to the masking signal. The masking sound generated by the audio speaker of the second transducer is generated simultaneously with the sound generated by the audio speaker of the first transducer, where the audio speaker of the first transducer is positioned in audio communication with a first ear of a patient and the audio speaker of the second transducer is positioned in audio communication with a second ear of the patient.

In some embodiments, the transducer may further include a second audio speaker positioned in communication with the transducer processor unit and the audiometer DSP unit may further be configured to generate masking signals responsive to a user input masking signal, convert the masking signals to a plurality of masking data packets, and interleave each of the plurality of masking data packets and the plurality of stimulus data packets, defining a plurality of interleaved data packets, where each interleaved data packet may include a header, at least two masking data packets, and at least two stimulus data packets. The audiometer baseband processing unit may further configured to receive the plurality of interleaved data packets from the audiometer DSP unit and generate a plurality of interleaved audiometer frames, each frame may include a packet of the plurality of interleaved data packets. The audiometer light-based transceiver is further configured to transmit the interleaved audiometer frames received from the audiometer baseband processing unit. The transducer may include a second audio speaker positioned in communication with the transducer processor unit and the transducer light-based transceiver is further configured to receive the plurality of interleaved audiometer frames from the audiometer light-based transceiver. The transducer baseband processing unit is further configured to receive the plurality of interleaved audiometer frames from the transducer light-based transceiver and extract the plurality of interleaved data packets from the audiometer frames, defining a plurality of extracted interleaved data packets. The transducer processor unit is further configured to: receive the plurality of extracted interleaved data packets from the transducer baseband processing unit, convert the plurality of extracted interleaved data packets into a masking audio signal and the patient stimulus signal. The second audio speaker is configured to receive the masking audio signal from the transducer processor unit and generate a masking sound responsive to the masking audio signal.

In some embodiments, the transducer processor unit is further configured to generate a plurality of transducer calibration data response packets responsive to the calibration data requests, the transducer calibration data response packets may include transducer calibration data. The transducer baseband processing unit is further configured to receive the plurality of transducer calibration data response packets and generate a plurality of transducer calibration frames, each transducer calibration frame may include a transducer calibration data packet. The transducer light-based transceiver is further configured to transmit the plurality of transducer calibration frames to the audiometer light-based transceiver. The audiometer light-based transceiver is further configured to receive the plurality of transducer calibration frames from the transducer light-based transceiver. The audiometer baseband processing unit is further configured to: receive the plurality of transducer calibration frames from the audiometer light-based transceiver and extract the plurality of transducer calibration data packets from the transducer frames. The audiometer DSP unit is further configured to receive the plurality of transducer calibration data packets, extract the transducer calibration data from the plurality of transducer calibration data packets, store the transducer calibration data, and generate the tone responsive to both of the stimulus configuration from the user input and the transducer calibration data.

One general aspect includes an audiometer system that includes an audiometer device may include an audiometer DSP unit configured to generate tone signals responsive to a user input signal, generate masking signals responsive to a user input masking signal, convert the tone signals to a plurality of stimulus data packets, convert the masking signals to a plurality of masking data packets, and arrange the stimulus data packets and masking data packets into time division multiplexed (TDM) data packets. The system also includes an audiometer baseband processing unit positioned in communication with the audiometer DSP unit and configured to convert the TDM data packets to a plurality of TDM audiometer frames; and an audiometer light-based transceiver positioned in communication with the audiometer baseband processing unit and configured to transmit the plurality of TDM audiometer frames. The system also includes a first transducer that may include a first transducer light-based transceiver positionable within a field of view of the audiometer light-based transceiver, the first transducer light-based transceiver configured to receive the plurality of TDM audiometer frames from the audiometer light-based transceiver, a first transducer baseband processing unit positioned in communication with the first transducer light-based transceiver and configured to receive the plurality of TDM audiometer frames from the first transducer light-based transceiver and convert the plurality of TDM audiometer frames to transducer TDM data packets. The system also includes a first transducer processor unit positioned in communication with the first transducer baseband processing unit and configured to receive the extracted TDM data packets from the first transducer baseband processing unit, extract the stimulus data packets from the transducer TDM data packets, defining extracted stimulus data packets, and convert the extracted stimulus data packets into a patient stimulus signal. The system also includes a first audio speaker positioned in communication with the transducer processor unit and configured to generate a sound responsive to the audio signal. The system also includes a second transducer may include a second transducer light-based transceiver positionable within a field of view of the audiometer light-based transceiver, the second transducer light-based transceiver configured to receive the plurality of TDM audiometer frames from the audiometer light-based transceiver, a second transducer baseband processing unit positioned in communication with the second transducer light-based transceiver and configured to receive the plurality of TDM audiometer frames from the second transducer light-based transceiver and extract the TDM data packets from the TDM audiometer frames, defining extracted TDM data packets. The system also includes a second transducer processor unit positioned in communication with the second transducer baseband processing unit and configured to receive the extracted TDM data packets from the second transducer baseband processing unit, extract the masking data packets from the extracted TDM data packets, defining extracted masking data packets, and convert the extracted masking data packets into a masking audio signal. The system also includes a second audio speaker positioned in communication with the second transducer processor unit and configured to receive the masking audio signal from the transducer processor unit and generate a masking sound responsive to the masking audio signal. The system also includes where the sound generated by the audio speaker of the second transducer is generated simultaneously with the sound generated by the audio speaker of the first transducer.

The system also includes where the audio speaker of the first transducer is positioned in audio communication with a first ear of a patient. The system also includes where the audio speaker of the second transducer is positioned in audio communication with a second ear of the patient. Other embodiments of this aspect include corresponding computer systems, apparatus, and computer programs recorded on one or more computer storage devices, each configured to perform the actions of the methods.

BRIEF DESCRIPTION OF THE DRAWINGS

Some embodiments of the present invention are illustrated as an example and are not limited by the figures of the accompanying drawings, in which like references may indicate similar elements.

DETAILED DESCRIPTION OF THE INVENTION

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Those of ordinary skill in the art realize that the following descriptions of the embodiments of the present invention are illustrative and are not intended to be limiting in any way. Other embodiments of the present invention will readily suggest themselves to such skilled persons having the benefit of this disclosure. Like numbers refer to like elements throughout.

Although the following detailed description contains many specifics for the purposes of illustration, anyone of ordinary skill in the art will appreciate that many variations and alterations to the following details are within the scope of the invention. Accordingly, the following embodiments of the invention are set forth without any loss of generality to, and without imposing limitations upon, the claimed invention.

In this detailed description of the present invention, a person skilled in the art should note that directional terms, such as "above," "below," "upper," "lower," and other like terms are used for the convenience of the reader in reference to the drawings. Also, a person skilled in the art should notice this description may contain other terminology to convey position, orientation, and direction without departing from the principles of the present invention.

Furthermore, in this detailed description, a person skilled in the art should note that quantitative qualifying terms such as "generally," "substantially," "mostly," and other terms are used, in general, to mean that the referred to object, characteristic, or quality constitutes a majority of the subject of the reference. The meaning of any of these terms is dependent upon the context within which it is used, and the meaning may be expressly modified.

Figure 1:
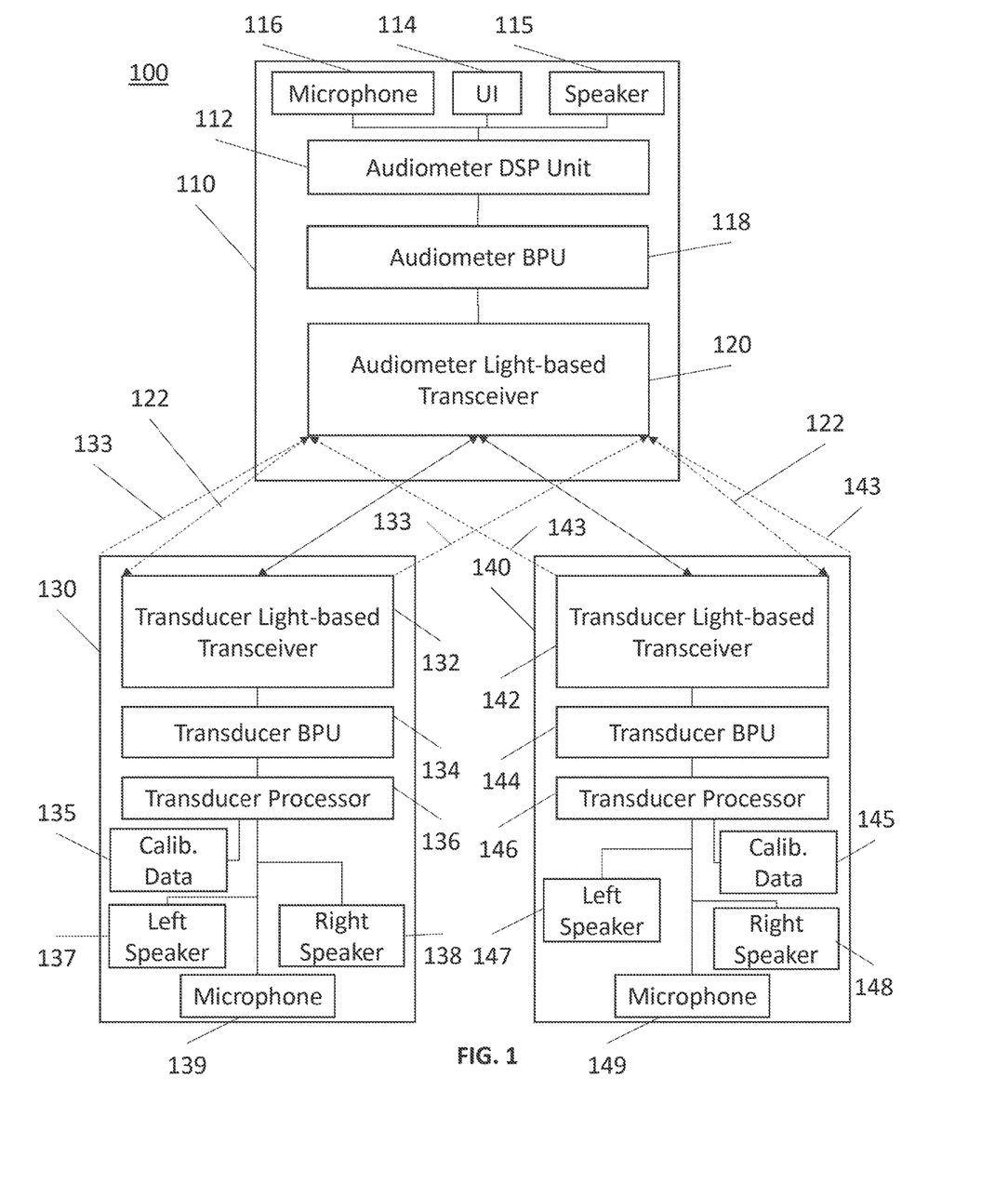
FIG. 1 is a schematic view of a light-based audiometry system according to an embodiment of the invention.

An embodiment of the invention, as shown and described by the various figures and accompanying text, provides an audiometer system utilizing a light-based communication system between the audiometer device and the one or more devices the patient interacts with. Referring now to FIG. 1, an audiometer system 100 according to an embodiment of the invention is presented. The audiometer system 100 comprises an audiometer device 110. The audiometer device 110 may be a device capable of generating stimulus signals to be used in an audiometric screening process performed on a patient. The audiometer device 110 may comprise an audiometer digital signal processor (DSP) unit 112. The DSP unit 112 may be any DSP microprocessor chip or other microprocessor chip or core capable of performing DSP functions as are known in the art. The DSP unit 112 may be configured to generate stimulus signals for use in an audiometry test responsive to user input signals. The stimulus signals may be in the form of a signal stream. The signal may be generated in response to an input from a user. Such an input may come from any input device as is known in the art, including user input devices 114 such as mice, keyboards, and multi-button control or touch devices, a microphone 116, and any other device that may generate a signal that may be processed by the DSP unit 112. In some embodiments, the DSP unit 112 may be connected to a user computerized device, such as a desktop or laptop computer, a smartphone, or other computer device. In some embodiments, the user interface 114 and/or microphone 116 may be comprised by the audiometer device 110. In some embodiments, the user interface 114 and/or the microphone 116 may be discrete devices not comprised by the audiometer device 110 and instead are connected to and operable with the audiometer device 110. The input may be at least one of an input audio signal and an input speech signal, and may define an input signal.

Furthermore, the DSP unit 112 may be configured to generate a plurality of masking signals. The masking signals may be generated responsive to at least one of a user input masking signal and the stimulus signals. In some embodiments, the user input stimulus signal and the user input masking signal may be received by the DSP unit as a consolidated test signal. The masking signals may be in the form of a signal stream.

Figure 2:
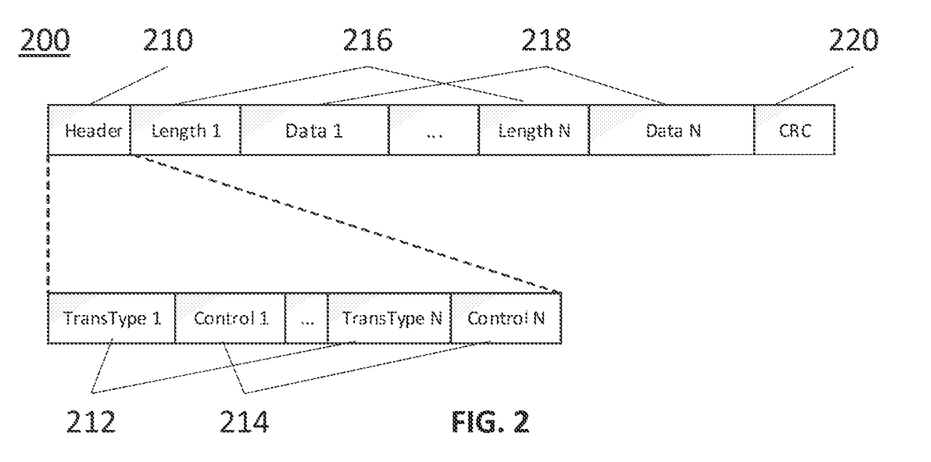
FIG. 2 is a graphical representation of data packets used in a light-based audiometry system according to an embodiment of the invention.

The DSP unit 112 may be configured to convert the stimulus signals and the masking signals received from the user input signal to a plurality of stimulus data packets and a plurality of masking data packets, respectively. The stimulus and masking data packets may be packetized data that is configured to facilitate the transmission thereof. In some embodiments, the data packets may be configured as TDM packets. Referring now to FIG. 2, additional details regarding the format of each TDM data packet 200 is presented. Each TDM data packet 200 may comprise a header 210 containing information that details the content of the data packet 200. The header 210 may comprise a plurality of transducer type data segments 212 and a plurality of control data segments 214. Each transducer type data segment 212 may identify the type of transducer, the $1^{st}$, $2^{nd}$, $3^{rd}$, through $N^{th}$ transducer. The type of transducer indicated may be any type as is known in the art, including, but not limited to air conduction (AC), bone conduction (BC), high frequency (HF), and insert phone (INS). Each data packet 200 may further comprise a plurality of length fields 216 and a plurality of data fields 218, with each length field indicating a length of an associated data field, i.e. length field 1 defining the length of data field 1, length field n defining the length of data field n. The data packet may be structured such that each length field i immediately precedes its associated data field i. The data packet 200 may further comprise a cyclic redundancy check field 220 containing a check value that may determine whether any data corruption errors have occurred in transmission of the data packet 200, as is known in the art.

The plurality of stimulus and masking data packets may be sent to the audiometer baseband processing unit (BPU) 118. The audiometer BPU 118 may be configured to convert the stimulus data packets into a plurality of stimulus audiometer frames and to convert the masking data packets into a plurality of masking audiometer frames. Each frame may be a data transmission unit comprising a stimulus data packet or a masking data packet. In some embodiments, the frames may be structured to conform to time-division multiplexing (TDM.

The audiometer device 110 may further comprise an audiometer light-based transceiver 120. The audiometer light-based transceiver 120 may be a device operable to transmit data via electromagnetic radiation (EMR) within at least one of the ultraviolet spectrum, i.e. having a wavelength within a range from 10 nanometers (nm) to 400 nm, the visible spectrum, i.e. having a wavelength within a range from 400 nm to 750 nanometers, and the infrared spectrum, i.e. having a wavelength within a range from 700 nm to 1 millimeter (mm), thereby enabling optical wireless communication. The audiometer light-based transceiver 120 may comprise a light-emitting device operable to emit the above-described EMR in a pulsed manner to enable optical wireless communication and an optical sensor operable to measure EMR within one or more of the above wavelength ranges. The light-emitting device may be any EMR-emitting device as is known in the art, including, but not limited to, light-emitting diodes (LEDs), laser diodes, and the like. In some embodiments, the audiometer light-based transceiver may comply with known optical wireless communication methodologies, standards, and protocols, including, but not limited to, visible light communication (VLC), Li-Fi, and any other standard or protocol as is known in the art.

The audiometer light-based transceiver 120 may be positioned in communication with the audiometer BPU 118. The audiometer light-based transceiver 120 may be configured to receive the plurality of stimulus frames and the plurality of masking frames from the audiometer BPU 118. Furthermore, the audiometer light-based transceiver 120 may be configured to transmit the stimulus and masking audiometer frames generated by the audiometer BPU 118. The transmission may be a light-based transmission conforming with any of the light-based transmission standards and protocols described above or are otherwise known in the art. Transmission may be effectuated by emitting light into a field of view 122 of the audiometer light-based transceiver 120. The field of view may be understood as a region with a direct line-of-sight with the audiometer light-based transceiver 120, such that there are no intervening structures or bodies between the audiometer light-based transceiver 120 and the transceivers within the field of view 122 of the audiometer light-based transceiver 120 may receive the transmissions therefrom.

In some embodiments, the audiometer light-based transceiver 120 may be configured to perform an alignment process. The alignment process may be configured to produce a test optical emission to locate one or more receiving devices, e.g. transducer devices as described below, and align the light-emitting devices described above such that the field of view 122 encompasses the located receiving devices. In some embodiments, the audiometer light-based transceiver 120 may comprise an alignment light-emitting device (not shown) operable to emit a coherent optical signal that may be utilized in the location of such receiving devices. Such a device may be a laser, including laser diodes, as are known in the art. The alignment light-emitting device may emit EMR that may be reflected from a receiving device and sensed by the audiometer light-based transceiver 120 and, based on the characteristics of the reflected EMR, such as the phase of the incident reflected EMR and the time of flight of the same, may determine the location of the receiving device and identify a field of view that encompasses the determined location. Accordingly, the audiometer light-based transceiver may comprise an optical sensor (not shown) configured to sense and measure the reflected EMR. Types of optical sensors include, but are not limited to, photoconductive devices, photovoltaic devices, photodiodes, and phototransistors. In an alternative embodiment, the alignment process may comprise determining a relative angle between the audiometer light-based transceiver 120 a geometric normal of an optical receiver of the receiving device in the field of view 122. Additional details about such an alignment process are known in the art, as disclosed in *Visible Light Communication, Networking, and Sensing: A Survey, Potential and Challenges* by Pathak et al., IEEE COMMUNICATIONS SURVEYS & TUTORIALS, Vol. 14, No. 4, Fourth Quarter 2015, the content of which is incorporate herein by reference except to the extent disclosure therein is inconsistent with disclosure herein.

The audiometer system 100 may further comprise one or more transducer devices. In the present embodiment, the audiometer system 100 comprises a first transducer device 130 and a second transducer device 140. Each transducer device 130, 140 comprises a transducer light-based transceiver 132, 142, a transducer baseband processing unit (BPU) 134, 144, and a transducer processor 136, 146. The transducer light-based transceivers 132, 142 may be configured to be positionable within the field of view of the audiometer light-based transceiver 120 and receive and sense transmissions from the audiometer light-based transceiver 120. Accordingly, each transducer light-based transceiver 132, 142 may comprise an optical sensor (not shown) configured to sense and measure light emitted from the audiometer light-based transceiver 120. Types of optical sensors include, but are not limited to, photoconductive devices, photovoltaic devices, photodiodes, and phototransistors. The transducer light-based transceivers 132, 142 may generate a signal responsive to the transmission from the audiometer light-based transceiver 120 sensed thereby, the sensed transmissions being the stimulus and masking audiometer frames. To generate such a signal, the transducer light-based transceivers 132, 134 may comprise an amplifier and an analog-to-digital converter (ADC) (not shown), whereby the signal is generated by amplifying the output of the optical sensor with the amplifier and using the ADC to convert the amplified analog signal generated by the amplifier into a digital signal. Any amplifier and ADC as is known in the art is contemplated and included in the scope of the invention, and the invention is not limited to any particular type of amplifier or ADC.

The transducer BPUs 134, 144 may be positioned in communication with the transducer light-based transceivers 132, 142 and be configured to receive the stimulus and masking audiometer frames received thereby. The transducer BPUs 134, 144 may further be configured to convert the stimulus and masking audiometer frames into extracted stimulus and masking data packets, such that a plurality of stimulus data packets and a plurality of masking data packets are extracted from the respective frames.

The transducer processors 136, 146 may be positioned in communication with the transducer BPUs 134, 144 and be configured to receive the pluralities of stimulus data packets and masking data packets extracted thereby. The transducer processors 136, 146 may further be configured to convert the pluralities of stimulus data packets and masking data packets into a respective patient stimulus signal and a patient masking signal. The patient stimulus and masking signals may be digital signals capable of being used to generate audio signals to be heard by a patient undergoing an audiometry test.

The transducer devices 130, 140 may further comprise one or more speakers, as in the present embodiment, left speakers 137, 147 and right speakers 138, 148. The speakers 137, 138, 147, 148 may be positioned in communication with the transducer processors 136, 146 and configured to receive the patient stimulus and/or masking signals and generate audible sounds responsive thereto. The characteristics of the audible sounds generated may be defined by the data comprised by and/or the characteristics of the patient stimulus and masking signals. Such characteristics include, but are not limited to, frequency, intensity, pitch, tone, sounds pressure, and any other characteristic or parameter of sound as is known in the art. In some embodiments, a single set of left and right speakers may be present, and each of the transducer processors 136, 146 may be positioned in communication therewith and operable to transmit the patient stimulus and masking signals thereto.

The transducer devices 130, 140 may further comprise one or more transducer input devices 139, 149. The transducer input devices 139, 149 may be positioned in communication with the transducer processors 136, 146 and configured to receive an input from the patient to which the audiometry test is administered, defining a received patient input. The type of input received by the transducer input devices 139, 149 may depend on the type of device. For example, in some embodiments, the transducer input devices 139, 149 may be microphones and the patient input may be an audible signal produced by the patient, such as the patient speaking, tapping, or otherwise generating sound. In other embodiments, the transducer input devices 139, 149 may be a button, keyboard, switch, or other physically manipulable device/actuable tactile device, or a capacitive, resistive, optical, or other sensing device that the patient may manipulate responsive to an audible signal generated by one or more of the left and right speakers 137, 138, 147, 148. The transducer input devices 139, 149 may be operable to generate a signal responsive to the user input, defined as a patient response signal, that is received by the transducer processors 136, 146. Additionally, in some embodiments, a single transducer input device may be present. In such embodiments, the single transducer input device may be positioned in communication with one or both of the transducer processors 136, 146.

The transducer processors 136, 146 may further be configured to receive the patient response signal from the transducer input devices 139, 149, generate a patient response data stream from the patient response signal, and generate a plurality of transducer data packets from the response data stream, each transducer data packet of the plurality of transducer data packets comprising data comprised by the patient response data stream. In some embodiments, the plurality of transducer data packets may be one of transducer stimulus data packets where the transducer 130, 140 received the stimulus audiometer frames and transducer masking data packets where the transducer 130, 140 received masking audiometer frames. The transducer processors 136, 146 may further be configured to transmit the plurality of transducer data packets to the transducer BPUs 134, 144. The transducer BPUs 134, 144 may further be configured to receive the plurality of transducer data packets from the transducer processors 136, 146 and generate a plurality of transducer frames, where each transducer frame comprises a transducer data packet. The plurality of transducer frames may be configured to be transmissible via light-based communication as described above. The transducer BPUs 134, 144 may further be configured to transmit the plurality of transducer frames to the transducer light-based transceivers 132, 142.

The transducer light-based transceivers 132, 142 may further be configured to receive the plurality of transducer frames from the transducer BPUs 134, 144 and transmit the plurality of transducer frames to the audiometer light-based transceiver 120. Each transducer light-based transceiver 132, 142 may be configured to transmit the plurality of transducer frames via electromagnetic radiation (EMR) within at least one of the ultraviolet spectrum, i.e. having a wavelength within a range from 10 nanometers (nm) to 400 nm, the visible spectrum, i.e. having a wavelength within a range from 400 nm to 750 nanometers, and the infrared spectrum, i.e. having a wavelength within a range from 700 nm to 1 millimeter (mm), thereby enabling optical wireless communication. The transducer light-based transceivers 132, 142 may each comprise a light-emitting device operable to emit the above-described EMR in a pulsed manner to enable optical wireless communication and an optical sensor operable to measure EMR within one or more of the above wavelength ranges. The light-emitting device may be any EMR-emitting device as is known in the art, including, but not limited to, light-emitting diodes (LEDs), laser diodes, and the like. In some embodiments, the audiometer light-based transceiver may comply with known optical wireless communication methodologies, standards, and protocols, including, but not limited to, visible light communication (VLC), Li-Fi, and any other standard or protocol as is known in the art.

In some embodiments, the transducer light-based transceivers 132, 142 may be configured to perform an alignment process. The alignment process may be configured to produce a test optical emission to locate one or more receiving devices, e.g. transducer devices as described below, and align the light-emitting devices described above such that the fields of view 133, 143 encompasses the located receiving devices. In some embodiments, the transducer light-based transceivers 132, 142 may comprise an alignment light-emitting device (not shown) operable to emit a coherent optical signal that may be utilized in the location of such receiving devices, e.g. the audiometer light-based transceiver 120. Such a device may be a laser, including laser diodes, as are known in the art. The alignment light-emitting device may emit EMR that may be reflected from a receiving device and sensed by the audiometer light-based transceiver 120 and, based on the characteristics of the reflected EMR, such as the phase of the incident reflected EMR and the time of flight of the same, may determine the location of the receiving device and identify a field of view that encompasses the determined location. Accordingly, the transducer light-based transceivers 132, 142 may utilize the optical sensor described hereabove to detect the emitted alignment EMR. Similar to alignment of the audiometer light-based transducer 120 described hereinabove, the transducer light-based transceivers 132, 142 may alternatively be aligned by calculating an angle between the transceivers and a geometric normal of the audiometer light-based transducer 120.

The transducer light-based transceivers 132, 142 may be configured to transmit the plurality of transducer frames by a light-based transmission conforming with any of the light-based transmission standards and protocols described above or are otherwise known in the art. Transmission may be effectuated by emitting light into a field of view 133, 143 of the transducer light-based transceivers 132, 142. The fields of view may be understood as a region with a direct line-of-sight with the transducer light-based transceivers 132, 142, such that there are no intervening structures or bodies between the transducer light-based transceivers 132, 142 and the transceivers within the fields of view 133, 143 of the transducer light-based transceivers 132, 142 may receive the transmissions therefrom.

The audiometer light-based transceiver 120 may further be configured to receive the plurality of transducer frames from the transducer light-based transceivers 132, 142. The plurality of transducer frames may be received using the optical sensor described above. The audiometer light-based transceiver 120 may further be configured to transmit the plurality of transducer frames to the audiometer baseband processing unit 118. In turn, the audiometer baseband processing unit 118 may be configured to receive the plurality of transducer frames from the audiometer light-based transceiver 120, extract the plurality of transducer data packets from the transducer frames, defining a plurality of extracted transducer data packets, and transmit the plurality of extracted transducer data packets to the audiometer DSP unit 116. Further, the audiometer DSP unit 116 may further be configured to receive the plurality of extracted transducer data packets from the audiometer baseband processing unit 118, generate a received patient response signal stream from the plurality of extracted transducer data packets, convert the received patient response signal stream into an audio signal, defining a received patient audio signal, and transmit the received patient audio signal to a user playback device 115. The user playback device 115 may be any device operable to generate a playback response responsive to the received patient audio signal. The user playback device may, for example, be an electroacoustic loudspeaker, a microelectromechanical system (MEMS) microspeaker, a piezoelectric speaker, and any other audible sound-generating device as are known in the art. In some embodiments, the user playback device 115 may be a computerized device comprising such a loudspeaker, including, but not limited to, a desktop computer, a laptop computer, a tablet device, a smartphone device, and the like.

While two transducers are disclosed in the present embodiment, it is contemplated and included within the scope of the invention that a single transducer device may be utilized. In such embodiments, the single transducer may receive both the stimulus and masking signals from the audiometer device and may selectively deliver those audio signals to the patient. In such embodiments, the audiometer DSP unit 112 may be configured to interleave the plurality of masking data packets and the plurality of stimulus data packets, defining a plurality of interleaved data packets. Each interleaved data packet may comprise a header, at least two masking data packets, and at least two stimulus data packets. Accordingly, each interleaved data packet may deliver both stimulus and masking data packets. Furthermore, the audiometer BPU 118 may be configured to receive the plurality of interleaved data packets and generate a plurality of interleaved audiometer frames, with each interleaved audiometer frame comprising a packet of the plurality of interleaved data packets. The plurality of interleaved audiometer frames may then be transmitted to the audiometer light-based transceiver 120, emitted thereby into the field of view 122, and be received by the transducer light-based transceiver 132. The transducer light-based transceiver 132 may further be configured to transmit the received plurality of interleaved audiometer frames to the transducer BPU 134 that may in turn be configured to receive the frames and extract the interleaved data packets from the audiometer frames, defining a plurality of extracted interleaved data packets. The transducer BPU 134 may then transmit the plurality of extracted interleaved audiometer packets to the transducer processing unit 136 that may in turn convert the plurality of extracted interleaved data packets into respective patient stimulus audio signal and a patient masking audio signal. The transducer processing unit 136 may then selectively playback the patient stimulus and masking audio signals on the playback devices, e.g. the left and right speakers 137, 138 by generating stimulus and masking sounds thereon to be heard by the patient.

Additionally, in some embodiments, the audiometer DSP unit 112 may be configured to arrange the pluralities of stimulus and masking data packets into time-division multiplexed (TDM) packets. Such TDM packets may be converted to TDM audiometer frames, transmitted to the transducers 130, 140, and accordingly used as the previously-described data packets in conducting an audiometry test, with the stimulus and masking signals being extracted from the TDM audiometer frames by the transducers 130, 140 and played to the patient.

In some embodiments, the transducer devices 130, 140 may comprise calibration data 135, 145. The calibration data 135, 145 may comprise information that facilitates the accurate recreation and representation of the desired stimulus or masking signal on the left and/or right speakers 137, 138, 147, 148. In such embodiments, the audiometer DSP unit 112 may further be configured to generate a calibration data request comprising a plurality of calibration data request packets and transmit the plurality of calibration data request packets to the audiometer BPU 118. The audiometer BPU 118 may in turn be configured to receive the plurality of calibration data request packets, generate a plurality of calibration audiometer frames, each calibration audiometer frame comprising a packet of the plurality of calibration data request packets and transmit the plurality of calibration audiometer frames to the audiometer light-based transceiver 120. The audiometer light-based transceiver 120 may further be configured to receive the plurality of calibration audiometer frames and transmit them as pulsed light into the field of view 122 as described above.

Further, the transducer light-based transceivers 132, 142 may further be configured to receive the plurality of calibration audiometer frames from the audiometer light-based transceiver 120 and transmit them to the transducer BPUs 134, 144. The transducer BPUs 134, 144 may further be configured to receive the plurality of calibration audiometer frames from the transducer light-based transceivers 132, 142, extract the calibration data request packets from the calibration audiometer frames, defining a plurality of extracted calibration data request packets, and transmit the plurality of extracted calibration data requests to the transducer processor unit 136, 146. The transducer processor units 136, 146 may further configured to receive the plurality of extracted calibration data request packets, parse the plurality of extracted calibration data request packets to extract the calibration data request therefrom, and read the calibration data 135, 145 stored in the transducer 130, 140. The calibration data 135, 145 may then be transmitted to the transducer processors 136, 146, which may further be configured to receive the calibration data 135, 145, generate a plurality of calibration data packets therefrom, and transmit the plurality of calibration data packets to the transducer BPU 134, 144. In turn, the transducer BPU 134, 144 may be configured to receive the plurality of calibration data packets, generate a plurality of calibration data frames responsive thereto, with each calibration data frame comprising a calibration data packet of the plurality of calibration data packets, and transmit the plurality of calibration data frames to the transducer light-based transceivers 132, 142. The transducer light-based transceivers 132, 142 may further be configured to transmit the plurality of calibration data frames into their respective fields of view 133, 143 as described above, and be received by the audiometer light-based transceiver 120. The audiometer light-based transceiver 120 may in turn be configured to transmit the plurality of calibration data frames to the audiometer BPU 118. The audiometer BPU 118 may be configured to, upon receiving the plurality of calibration data frames, extract the plurality of calibration data packets from the plurality of calibration data frames, defining a plurality of extracted calibration data packets, and transmit the plurality of extracted calibration data packets to the audiometer DSP unit 112. The audiometer DSP unit 112 may be configured to receive the plurality of extracted calibration data packets and generate one or more of the stimulus signal and the masking signal responsive to the extracted calibration data packets, specifically the data comprised thereby. It is contemplated and included within the scope of the invention that the calibration data request and response may be done serially/sequentially or in parallel/simultaneously, such as in a TDM format.

The calibration data may indicate the fidelity with which the transducers 130, 140 will recreate the audible sound indicated by the stimulus and masking signals, and those signals may be generated to compensate for any losses in fidelity that may result from the playback of audio signals transmitted to the transducers 130, 140. In some embodiments, the calibration data may comprise one or more equalizing filter coefficients. The one or more equalizing filter coefficients may be applied to the stimulus signal received from the user to ensure the sound produced thereby on the transducer devices 130, 140 matches the user's stimulus selection that generated the stimulus signal.

Some of the illustrative aspects of the present invention may be advantageous in solving the problems herein described and other problems not discussed which are discoverable by a skilled artisan.

While the above description contains much specificity, these should not be construed as limitations on the scope of any embodiment, but as exemplifications of the presented embodiments thereof. Many other ramifications and variations are possible within the teachings of the various embodiments. While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the scope of the appended claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

Thus the scope of the invention should be determined by the appended claims and their legal equivalents, and not by the examples given.

What is claimed is:

1. An audiometer system comprising:
   an audiometer device comprising:
      an audiometer digital signal processing (DSP) unit configured to:
         generate stimulus signals responsive to a user input signal; and
         convert the stimulus signals to a plurality of stimulus data packets;
      an audiometer baseband processing unit positioned in communication with the audiometer DSP unit and configured to convert the stimulus data packets to a plurality of stimulus audiometer frames; and
      an audiometer light-based transceiver positioned in communication with the audiometer baseband processing unit and configured to transmit the plurality of stimulus audiometer frames;
   a transducer comprising:
      a transducer light-based transceiver positionable within a field of view of the audiometer light-based transceiver, the transducer light-based transceiver configured to receive the plurality of stimulus audiometer frames from the audiometer light-based transceiver;
      a transducer baseband processing unit positioned in communication with the transducer light-based transceiver and configured to convert the plurality of stimulus audiometer frames to a plurality of extracted stimulus data packets;
      a transducer processor unit positioned in communication with the transducer baseband processing unit and configured to convert the plurality of extracted stimulus data packets into a patient stimulus signal; and
      an audio speaker positioned in communication with the transducer processor unit and configured to generate a sound responsive to the patient stimulus signal.

2. The audiometer system of claim 1 wherein:
   the transducer further comprises:
      a transducer input device positioned in communication with the transducer processor unit and configured to:
         receive a patient input from the patient, defining a received patient input; and
         generate a patient response signal from the received patient input;
   the transducer processor unit is further configured to convert the patient response signal to a plurality of transducer data packets;
   the transducer baseband processing unit is further configured to generate a plurality of transducer frames, each transducer frame comprising a transducer data packet;
   the transducer light-based transceiver is further configured to transmit the plurality of transducer frames to the audiometer light-based transceiver;
   the audiometer light-based transceiver is further configured to receive the plurality of transducer frames from the transducer light-based transceiver;

the audiometer baseband processing unit is further configured to convert the plurality of transducer frames to a received patient audio signal stream; and
the audiometer DSP unit is further configured to:
  convert the received patient audio signal stream to an audio signal, defining a received patient audio signal; and
  transmit the received patient audio signal to a user playback device.

3. The audiometer system of claim 1 wherein the transducer light-based transceiver is a first transducer light-based transceiver and the transducer is a first transducer, the audiometer system further comprising:
  a second transducer comprising:
    a second transducer light-based transceiver positionable within a field of view of the audiometer light-based transceiver, the second transducer light-based transceiver configured to receive the plurality of audiometer frames from the audiometer light-based transceiver;
    a second transducer baseband processing unit positioned in communication with the second transducer light-based transceiver and configured to convert the plurality of audiometer frames to a second plurality of extracted stimulus data packets;
    a second transducer processor unit positioned in communication with the second transducer baseband processing unit and configured to convert the second plurality extracted stimulus data packets into a second patient stimulus signal; and
    a second audio speaker positioned in communication with the transducer processor unit and configured to:
      receive the second patient stimulus signal from the transducer processor unit; and
      generate a sound responsive to the second patient stimulus signal.

4. The audiometer system of claim 3 wherein the second transducer baseband processing unit is further configured to:
  receive the plurality of audiometer frames from the transducer light-based transceiver; and
  extract the stimulus data packets from the audiometer frames, defining extracted stimulus data packets.

5. The audiometer of claim 3 wherein:
the audiometer DSP unit is further configured to generate a calibration data request comprising a plurality of calibration data request packets;
the audiometer baseband processing unit is further configured to:
  receive the plurality of calibration data request packets from the audiometer DSP unit; and
  generate a plurality of calibration audiometer frames, each frame comprising a packet of the calibration data request packets;
the audiometer light-based transceiver is further configured to transmit the plurality of calibration audiometer frames received from the audiometer baseband processing unit;
the transducer light-based transceiver is further configured to receive the plurality of calibration audiometer frames from the audiometer light-based transceiver;
the transducer baseband processing unit is further configured to:
  receive the plurality of calibration audiometer frames from the transducer light-based transceiver; and
  extract the calibration data request packets from the calibration audiometer frames, defining a plurality of extracted calibration data request packets; and
the transducer processor unit is further configured to:
  receive the plurality of extracted calibration data request packets;
  parse the plurality of extracted calibration data request packets to extract the calibration data request therefrom; and
  read the calibration data stored in the transducer.

6. The audiometer system of claim 1 wherein:
the audiometer DSP unit is further configured to:
  receive at least one of an input audio signal and an input speech signal, defining an input signal;
  generate a stimulus stream responsive to the input signal; and
  generate a plurality of packets from the stimulus stream, defining stimulus data packets;
the audiometer baseband processing unit is further configured to:
  receive the stimulus data packets from the audiometer DSP unit; and
  generate a plurality of stimulus audiometer frames, each frame comprising a packet of the stimulus data packets; and
the transducer baseband processing unit is further configured to:
  receive the plurality of stimulus audiometer frames from the transducer light-based transceiver; and
  extract the stimulus data packets from the stimulus audiometer frames, defining extracted stimulus data packets.

7. The audiometer system of claim 6 wherein:
the transducer further comprises:
  a transducer input device positioned in communication with the transducer processor unit and configured to:
    receive a patient input from the patient, defining a received patient input; and
    generate a patient response signal from the received patient input;
the transducer processor unit is further configured to:
  receive the patient response signal from the transducer input device;
  generate a response data stream from the patient response signal; and
  generate a plurality of transducer data packets from the response data stream;
the transducer baseband processing unit is further configured to:
  receive the plurality of transducer data packets; and
  generate a plurality of transducer frames, each transducer frame comprising a transducer data packet;
the transducer light-based transceiver is further configured to transmit the plurality of transducer frames to the audiometer light-based transceiver;
the audiometer light-based transceiver is further configured to receive the plurality of transducer frames from the transducer light-based transceiver;
the audiometer baseband processing unit is further configured to:
  receive the plurality of transducer frames from the audiometer light-based transceiver; and
  extract the plurality of transducer data packets from the transducer frames, defining a plurality of extracted transducer data packets;
the audiometer DSP unit is further configured to:
  receive the plurality of extracted transducer data packets from the audiometer baseband processing unit;
  generate a received patient response signal stream from the plurality of extracted transducer data packets;

convert the received patient response signal stream into an audio signal, defining a received patient audio signal; and transmit the received patient audio signal to a user playback device.

8. The audiometer system of claim 7 wherein the transducer input device is at least one of an actuatable tactile device and a microphone.

9. The audiometer system of claim 7 wherein the user playback device is at least one of an audio speaker and a computerized device.

10. The audiometer system of claim 1 wherein:

the transducer light-based transceiver is a first transducer light-based transceiver and the transducer is a first transducer;

the audiometer DSP unit is further configured to:
generate masking signals responsive to a user input masking signal; and
convert the masking signals to a plurality of masking data packets;

the audiometer baseband processing unit is further configured to:
receive the masking data packets from the audiometer DSP unit; and
generate a plurality of masking audiometer frames, each frame comprising a packet of the masking data packets; and the audiometer light-based transceiver is further configured to transmit the masking audiometer frames received from the audiometer baseband processing unit;

the audiometer system further comprising:
a second transducer comprising:
a second transducer light-based transceiver positionable within a field of view of the audiometer light-based transceiver, the second transducer light-based transceiver configured to receive the plurality of masking audiometer frames from the audiometer light-based transceiver;
a second transducer baseband processing unit positioned in communication with the second transducer light-based transceiver and configured to:
receive the plurality of masking audiometer frames from the transducer light-based transceiver; and
extract the masking data packets from the audiometer frames, defining extracted masking data packets; and
a second transducer processor unit positioned in communication with the second transducer baseband processing unit and configured to:
receive the extracted masking data packets and convert the extracted masking data packets into a masking signal; and
a second audio speaker positioned in communication with the second transducer processor unit and configured to:
receive the masking signal from the transducer processor unit; and
generate a masking sound responsive to the masking signal;

wherein the masking sound generated by the audio speaker of the second transducer is generated simultaneously with the sound generated by the audio speaker of the first transducer;

wherein the audio speaker of the first transducer is positioned in audio communication with a first ear of a patient; and wherein the audio speaker of the second transducer is positioned in audio communication with a second ear of the patient.

11. The audiometer system of claim 1 wherein:

the transducer further comprises a second audio speaker positioned in communication with the transducer processor unit;

the audiometer DSP unit is further configured to:
generate masking signals responsive to a user input masking signal;
convert the masking signals to a plurality of masking data packets; and
interleave each of the plurality of masking data packets and the plurality of stimulus data packets, defining a plurality of interleaved data packets, wherein each interleaved data packet comprises a header, at least one masking data packets, and at least one stimulus data packets;

the audiometer baseband processing unit is further configured to:
receive the plurality of interleaved data packets from the audiometer DSP unit; and
generate a plurality of interleaved audiometer frames, each frame comprising a packet of the plurality of interleaved data packets; and the audiometer light-based transceiver is further configured to transmit the interleaved audiometer frames received from the audiometer baseband processing unit;

the transducer further comprising a second audio speaker positioned in communication with the transducer processor unit;

the transducer light-based transceiver is further configured to receive the plurality of interleaved audiometer frames from the audiometer light-based transceiver;

the transducer baseband processing unit is further configured to:
receive the plurality of interleaved audiometer frames from the transducer light-based transceiver; and
extract the plurality of interleaved data packets from the audiometer frames, defining a plurality of extracted interleaved data packets; and the transducer processor unit is further configured to:
receive the plurality of extracted interleaved data packets from the transducer baseband processing unit;
convert the plurality of extracted interleaved data packets into a masking audio signal and the patient stimulus signal; and the second audio speaker is configured to:
receive the masking audio signal from the transducer processor unit; and
generate a masking sound responsive to the masking audio signal.

12. The audiometer of claim 11 wherein:

the transducer processor unit is further configured to:
generate a plurality of transducer calibration data response packets responsive to the calibration data requests, the transducer calibration data response packets comprising transducer calibration data;

the transducer baseband processing unit is further configured to:
receive the plurality of transducer calibration data response packets; and generate a plurality of transducer calibration frames, each transducer calibration frame comprising a transducer calibration data packet;
the transducer light-based transceiver is further configured to transmit the plurality of transducer calibration frames to the audiometer light-based transceiver;
the audiometer light-based transceiver is further configured to receive the plurality of transducer calibration frames from the transducer light-based transceiver;
the audiometer baseband processing unit is further configured to:
  receive the plurality of transducer calibration frames from the audiometer light-based transceiver;
  extract the plurality of transducer calibration data packets from the transducer frames;
the audiometer DSP unit is further configured to:
  receive the plurality of transducer calibration data packets;
  extract the transducer calibration data from the plurality of transducer calibration data packets;
  store the transducer calibration data; and
  generate the tone responsive to both of the stimulus configuration from the user input and the transducer calibration data.

13. An audiometer system comprising:
an audiometer device comprising:
  an audiometer digital signal processing (DSP) unit configured to:
    receive at least one of an input audio signal and an input speech signal, defining an input signal;
    generate a stimulus stream responsive to the input signal; and
    generate a plurality of packets from the stimulus stream, defining stimulus data packets;
  an audiometer baseband processing unit positioned in communication with the audiometer DSP unit and configured to:
    receive the stimulus data packets from the audiometer DSP unit; and
    generate a plurality of stimulus audiometer frames, each frame comprising a packet of the stimulus data packets; and
  an audiometer light-based transceiver positioned in communication with the audiometer baseband processing unit and configured to transmit the plurality of stimulus audiometer frames;
a transducer comprising:
  a transducer light-based transceiver positionable within a field of view of the audiometer light-based transceiver, the transducer light-based transceiver configured to receive the plurality of stimulus audiometer frames from the audiometer light-based transceiver;
  a transducer baseband processing unit positioned in communication with the transducer light-based transceiver and configured to:
    receive the plurality of stimulus audiometer frames from the transducer light-based transceiver; and
    extract the stimulus data packets from the stimulus audiometer frames, defining extracted stimulus data packets;
  a transducer processor unit positioned in communication with the transducer baseband processing unit and configured to convert the plurality of extracted stimulus data packets into a patient stimulus signal;
  an audio speaker positioned in communication with the transducer processor unit and configured to generate a sound responsive to the patient stimulus signal; and
  a transducer input device positioned in communication with the transducer processor unit and configured to:
    receive a patient input from the patient, defining a received patient input; and
    generate a patient response signal from the received patient input;
  wherein the transducer processor unit is further configured to convert the patient response signal to a plurality of transducer data packets;
  wherein the transducer baseband processing unit is further configured to generate a plurality of transducer frames, each transducer frame comprising a transducer data packet;
  wherein the transducer light-based transceiver is further configured to transmit the plurality of transducer frames to the audiometer light-based transceiver;
  wherein the audiometer light-based transceiver is further configured to receive the plurality of transducer frames from the transducer light-based transceiver;
  wherein the audiometer baseband processing unit is further configured to convert the plurality of transducer frames to a received patient response data packet; and
  wherein the audiometer DSP unit is further configured to:
    convert the received patient response data packet to an audio signal, defining a received patient audio signal; and
    transmit the received patient audio signal to a user playback device.

14. The audiometer system of claim 13 wherein the transducer input device is at least one of an actuatable tactile device and a microphone.

15. The audiometer system of claim 13 wherein the user playback device is at least one of an audio speaker and a computerized device.

16. The audiometer system of claim 13 wherein:
the transducer light-based transceiver is a first transducer light-based transceiver and the transducer is a first transducer;
the audiometer DSP unit is further configured to:
  generate masking signals responsive to a user input masking signal; and
  convert the masking signals to a plurality of masking data packets;
the audiometer baseband processing unit is further configured to:
  receive the masking data packets from the audiometer DSP unit; and
  generate a plurality of masking audiometer frames, each frame comprising a packet of the masking data packets; and
the audiometer light-based transceiver is further configured to transmit the masking audiometer frames received from the audiometer baseband processing unit;
the audiometer system further comprising:
  a second transducer comprising:
    a second transducer light-based transceiver positionable within a field of view of the audiometer light-based transceiver, the second transducer light-based transceiver configured to receive the plurality of masking audiometer frames from the audiometer light-based transceiver;

a second transducer baseband processing unit positioned in communication with the second transducer light-based transceiver and configured to:
receive the plurality of masking audiometer frames from the transducer light-based transceiver; and
extract the masking data packets from the audiometer frames, defining extracted masking data packets; and
a second transducer processor unit positioned in communication with the second transducer baseband processing unit and configured to:
receive the extracted masking data packets and convert the extracted masking data packets into a masking signal; and
a second audio speaker positioned in communication with the second transducer processor unit and configured to:
receive the masking signal from the transducer processor unit; and
generate a masking sound responsive to the masking signal;
wherein the masking sound generated by the audio speaker of the second transducer is generated simultaneously with the sound generated by the audio speaker of the first transducer;
wherein the audio speaker of the first transducer is positioned in audio communication with a first ear of a patient; and
wherein the audio speaker of the second transducer is positioned in audio communication with a second ear of the patient.

17. The audiometer system of claim 13 wherein:
the transducer further comprises a second audio speaker positioned in communication with the transducer processor unit;
the audiometer DSP unit is further configured to:
generate masking signals responsive to a user input masking signal;
convert the masking signals to a plurality of masking data packets; and
interleave each of the plurality of masking data packets and the plurality of stimulus data packets, defining a plurality of interleaved data packets, wherein each interleaved data packet comprises a header, at least one masking data packets, and at least one stimulus data packets;
the audiometer baseband processing unit is further configured to:
receive the plurality of interleaved data packets from the audiometer DSP unit; and
generate a plurality of interleaved audiometer frames, each frame comprising a packet of the plurality of interleaved data packets; and
the audiometer light-based transceiver is further configured to transmit the interleaved audiometer frames received from the audiometer baseband processing unit;
the transducer further comprising a second audio speaker positioned in communication with the transducer processor unit;
the transducer light-based transceiver is further configured to receive the plurality of interleaved audiometer frames from the audiometer light-based transceiver;
the transducer baseband processing unit is further configured to:
receive the plurality of interleaved audiometer frames from the transducer light-based transceiver; and
extract the interleaved data packets from the audiometer frames, defining extracted interleaved data packets; and
the transducer processor unit is further configured to:
receive the interleaved data packets from transducer baseband processing unit;
convert the interleaved data packets into a masking audio signal and the patient stimulus signal; and
the second audio speaker is configured to:
receive the masking audio signal from the transducer processor unit; and
generate a masking sound responsive to the masking audio signal.

18. The audiometer of claim 17 wherein:
the transducer processor unit is further configured to:
generate a plurality of transducer calibration data response packets responsive to the calibration data requests, the transducer calibration data response packets comprising transducer calibration data;
the transducer baseband processing unit is further configured to:
receive the plurality of transducer calibration data response packets; and
generate a plurality of transducer calibration frames, each transducer calibration frame comprising a transducer calibration data packet;
the transducer light-based transceiver is further configured to transmit the plurality of transducer calibration frames to the audiometer light-based transceiver;
the audiometer light-based transceiver is further configured to receive the plurality of transducer calibration frames from the transducer light-based transceiver;
the audiometer baseband processing unit is further configured to:
receive the plurality of transducer calibration frames from the audiometer light-based transceiver;
extract the plurality of transducer calibration data packets from the transducer frames;
the audiometer DSP unit is further configured to:
receive the plurality of transducer calibration data packets;
extract the transducer calibration data from the plurality of transducer calibration data packets;
store the transducer calibration data; and
generate the tone responsive to both of the stimulus configuration from the user input and the transducer calibration data.

19. The audiometer of claim 17 wherein:
the transducer light-based transceiver is a first transducer light-based transceiver and the transducer is a first transducer;
the audiometer DSP unit is further configured to:
generate masking signals responsive to a user input masking signal; and
convert the masking signals to a plurality of masking data packets;
the audiometer baseband processing unit is further configured to:
receive the masking data packets from the audiometer DSP unit; and
generate a plurality of masking audiometer frames, each frame comprising a packet of the masking data packets; and the audiometer light-based transceiver is further configured to transmit the masking audiometer frames received from the audiometer baseband processing unit;

the audiometer system further comprising:
  a second transducer comprising:
    a second transducer light-based transceiver positionable within a field of view of the audiometer light-based transceiver, the second transducer light-based transceiver configured to receive the plurality of masking audiometer frames from the audiometer light-based transceiver;
    a second transducer baseband processing unit positioned in communication with the second transducer light-based transceiver and configured to:
      receive the plurality of masking audiometer frames from the transducer light-based transceiver; and
      extract the masking data packets from the audiometer frames, defining extracted masking data packets; and
    a second transducer processor unit positioned in communication with the second transducer baseband processing unit and configured to:
      receive the extracted masking data packets and convert the extracted masking data packets into a masking signal; and
    a second audio speaker positioned in communication with the second transducer processor unit and configured to:
      receive the masking signal from the transducer processor unit; and
      generate a masking sound responsive to the masking signal;
  wherein the masking sound generated by the audio speaker of the second transducer is generated simultaneously with the sound generated by the audio speaker of the first transducer;
  wherein the audio speaker of the first transducer is positioned in audio communication with a first ear of a patient; and
  wherein the audio speaker of the second transducer is positioned in audio communication with a second ear of the patient.

20. An audiometer system comprising:
  an audiometer device comprising:
    an audiometer DSP unit configured to:
      generate tone signals responsive to a user input signal;
      generate masking signals responsive to a user input masking signal;
      convert the tone signals to a plurality of stimulus data packets;
      convert the masking signals to a plurality of masking data packets; and
      arrange the stimulus data packets and masking data packets into time division multiplexed (TDM) data packets;
    an audiometer baseband processing unit positioned in communication with the audiometer DSP unit and configured to convert the TDM data packets to a plurality of TDM audiometer frames; and
    an audiometer light-based transceiver positioned in communication with the audiometer baseband processing unit and configured to transmit the plurality of TDM audiometer frames;
  a first transducer comprising:
    a first transducer light-based transceiver positionable within a field of view of the audiometer light-based transceiver, the first transducer light-based transceiver configured to receive the plurality of TDM audiometer frames from the audiometer light-based transceiver;
    a first transducer baseband processing unit positioned in communication with the first transducer light-based transceiver and configured to:
      receive the plurality of TDM audiometer frames from the first transducer light-based transceiver; and
      convert the plurality of TDM audiometer frames to transducer TDM data packets;
    a first transducer processor unit positioned in communication with the first transducer baseband processing unit and configured to:
      receive the extracted TDM data packets from the first transducer baseband processing unit;
      extract the stimulus data packets from the transducer TDM data packets, defining extracted stimulus data packets; and
      convert the extracted stimulus data packets into a patient stimulus signal; and
    a first audio speaker positioned in communication with the transducer processor unit and configured to generate a sound responsive to the audio signal; and
  a second transducer comprising:
    a second transducer light-based transceiver positionable within a field of view of the audiometer light-based transceiver, the second transducer light-based transceiver configured to receive the plurality of TDM audiometer frames from the audiometer light-based transceiver;
    a second transducer baseband processing unit positioned in communication with the second transducer light-based transceiver and configured to:
      receive the plurality of TDM audiometer frames from the second transducer light-based transceiver; and
      extract the TDM data packets from the TDM audiometer frames, defining extracted TDM data packets; and
    a second transducer processor unit positioned in communication with the second transducer baseband processing unit and configured to:
      receive the extracted TDM data packets from the second transducer baseband processing unit;
      extract the masking data packets from the extracted TDM data packets, defining extracted masking data packets; and
      convert the extracted masking data packets into a masking audio signal; and
    a second audio speaker positioned in communication with the second transducer processor unit and configured to:
      receive the masking audio signal from the transducer processor unit; and
      generate a masking sound responsive to the masking audio signal;
  wherein the sound generated by the audio speaker of the second transducer is generated simultaneously with the sound generated by the audio speaker of the first transducer;

wherein the audio speaker of the first transducer is positioned in audio communication with a first ear of a patient; and wherein the audio speaker of the second transducer is positioned in audio communication with a second ear of the patient.

* * * * *